(12) United States Patent
Didillon et al.

(10) Patent No.: US 6,294,696 B1
(45) Date of Patent: *Sep. 25, 2001

(54) PROCESS FOR HYDROGENATING ORGANIC FUNCTIONS

(75) Inventors: Blaise Didillon; Fabienne Le Peltier, both of Rueil Malmaison (FR)

(73) Assignee: Institut Francais du Petrole, Rueil Malmaison Cedex (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/182,635

(22) Filed: Oct. 30, 1998

(30) Foreign Application Priority Data

Oct. 31, 1997 (FR) .................................. 97 13688

(51) Int. Cl.⁷ .................................................. C07C 209/00
(52) U.S. Cl. .......................... 564/422; 568/880; 502/170; 502/325
(58) Field of Search ............................ 564/422; 568/880; 502/170, 325

(56) References Cited

FOREIGN PATENT DOCUMENTS

| 2 653 118 | 4/1991 | (FR) . |
| 2 671 347 | 7/1992 | (FR) . |
| 2 694 286 | 2/1994 | (FR) . |

*Primary Examiner*—Paul J. Killos
(74) *Attorney, Agent, or Firm*—Millen, White, Zelano & Branigan, P.C.

(57) ABSTRACT

A process for hydrogenating organic compounds containing at least one function selected from aldehyde, ketone, ester, acid and nitro functions and/or containing an aromatic group is carried out in the presence of a catalyst comprising at least one support, at least one metal from group VIII of the periodic table and at least one additional element M selected from the group formed by germanium, tin, lead, rhenium, gallium, indium, gold, silver and thallium. The process is characterized in that the catalyst is prepared using a process in which said metal M is introduced in an aqueous solvent, in the form of at least one organometallic compound comprising at least one carbon-M bond.

22 Claims, No Drawings

PROCESS FOR HYDROGENATING ORGANIC FUNCTIONS

CROSS-REFERENCE TO RELATED APPLICATIONS

This application is related to concurrently filed applications entitled: Process for Preparing Catalysts for Use in Organic Compound Transformation Reactions (Attorney Docket No. PET 1702), based on French Application No. 97/13.684 filed Oct. 31, 1997, by Jean-Marie BASSET et al.; Process for Dehydrogenating Saturated Aliphatic Hydrocarbons to Olefinic Hydrocarbons (Attorney Docket No. PET 1703), based on French Application No. 97/13.685 filed Oct. 31, 1997, by Fabienne LE PELTIER et al.; Process for Selective Hydrogenation of Unsaturated Compounds (Attorney Docket No. PET 1706), based on French Application No. 97/13.687 filed Oct. 31, 1997, by Blaise DIDILLON et al.; and Catalytic Hydroreforming Process (Attorney Docket No. PET 1707), based on French Application No. 97/13.686 filed Oct. 31, 1997, by Fabienne LE PELTIER et al.

The present invention relates to a novel process for hydrogenating organic functions and/or an aromatic group in the presence of a catalyst comprising at least one support and at least one metal from group VIII of the periodic table. The catalyst comprises at least one additional element selected from germanium, tin, lead, rhenium gallium, indium, gold, silver and thallium. The catalyst can also contain a further metal selected from the group formed by alkali metals and/or a metalloid such as sulphur and/or any other chemical element such as a halogen or a halogen-containing compound.

Patents and publications demonstrating that the addition of promoters to a base metal improves the quality of catalysts exist in large numbers. Such elements are added in different forms such as salts or organometallic compounds. In general, catalysts which are more active or more selective and sometimes more stable than the corresponding monometallic catalyst are obtained. The manner in which such modifying agents are introduced is not inconsequential as it dictates the properties of the catalyst to a great extent.

Thus catalyst formulations used in processes for converting hydrocarbons have been the subject of a very large number of studies.

In the chemical field, the use of catalysts constituted by a plurality of metallic elements prepared by methods involving the use of an organometallic compound have also been widely described. Such catalysts are particularly suitable for selective hydrogenation of acid, ester, aldehyde, nitrogen-containing or olefinic functions. They have, for example, been described for the hydrogenation of aromatic ketones (French patent FR-A-2 964 286), of nitrogen-containing compounds (FR-A-2 671 347), and for the hydrogenation of aldehydes (FR-A-2 653 118).

The processes cited above describe the production of a catalyst using at least one organometallic compound of a metal M. The metal M is introduced in the form of at least one organometallic compound selected from the group formed by complexes, in particular carbonyl or polyketone complexes of metal M, and metal hydrocarbyls of metal M, such as alkyls, cycloalkyls, aryls, metal alkylaryls and metal arylalkyls.

Introducing the additional element M in the form of an organometallic compound leads to more effective catalysts but necessitates the use of an organic solvent. The impregnating solvent described in U.S. Pat. No. 4,548,918 is selected from the group formed by oxygen-containing organic solvents containing 2 to 8 carbon atoms per molecule, paraffin, naphthene or aromatic hydrocarbons essentially containing 6 to 15 carbon atoms per molecule, and halogen-containing oxygen-containing organic compounds containing 1 to 15 carbon atoms per molecule. Such solvents can be used alone or mixed together.

In the present invention we have discovered that particularly effective catalysts can be prepared by introducing metal M in the form of an organometallic complex which is soluble in an aqueous solvent. This represents a considerable advance as regards ease of use during production of the catalyst. Using large quantities of organic solvents has many disadvantages as regards safety (flammability, toxicity) and as regards costs.

In the present invention, the hydrocarbon conversion processes are operated at a temperature in the range 10° C. to 800° C., a pressure in the range 0.1 to 10 MPa, with an hourly space velocity in the range 0.1 to 100 volumes of liquid feed per hour per volume of catalyst.

The present invention thus provides a novel process for hydrogenating organic functions such as aldehyde, ketone, ester, acid, nitro or aromatic functions. The conditions used are conditions which are known to the skilled person, in particular an average temperature in the range 10° C. to 500° C., a pressure in the range 0.1 to 10 MPa and a space velocity in the range 0.5 to 50 volumes of liquid feed per hour per volume of catalyst.

The support for the catalyst of the invention comprises at least one refractory oxide which is generally selected from oxides of metals from groups IIA, IIIA, IIIB, IVA or IVB of the periodic table such as oxides of magnesium, aluminium, silicon, titanium, zirconium or thorium, used alone or mixed together or mixed with oxides of other elements from the periodic table. Charcoal can also be used. X, Y, mordenite, faujasite, ZSM-5, ZSM-4 or ZSM-8 type zeolites or molecular sieves can also be used, as well as mixtures of oxides of group IIA, IIIA, IIIB, IVA or IVB metals with a zeolitic material.

For hydrocarbon transformation reactions, alumina constitutes the preferred support, the specific surface area of which is advantageously in the range 5 to 400 $m^2$ per gram, preferably in the range 50 to 350 $m^2$ per gram.

Silica, charcoal and alumina constitute preferred supports for use in transforming organic functions.

In addition to a support, the catalyst of the invention includes:

a) at least one group VIII metal selected from iridium, nickel, palladium, platinum, rhodium and ruthenium. Platinum, palladium, ruthenium and rhodium are preferred metals. The percentage by weight is in the range 0.1% to 10%, preferably in the range 0.1% to 5%.

b) at least one additional element M selected from the group formed by germanium, tin, lead, rhenium, gallium, indium, gold, silver and thallium. Tin and germanium are preferred elements. The percentage by weight is in the range 0.01% to 10%, preferably in the range 0.02% to 5%. In some cases, at least two of the metals from this group can advantageously be used at once.

Depending on the application, the catalyst can also contain 0.2% to 3% by weight of a halogen or halogen-containing compound. It can also contain 0.2% to 3% by weight of an alkali or alkaline-earth metal.

The catalyst can be prepared using different procedures for impregnating the support and the invention is not limited to any specific impregnation procedure. When several solutions are used, intermediate drying and/or calcining steps can be carried out.

The additional element M can be introduced during production of the support. One method, for example, consists of blending the moist powdered support with catalyst precursors and then forming and drying. The group VIII metal, additional metal M, optional halogen or halogen-containing compound, optional alkali or alkaline-earth metal, and optional metalloid, can be introduced simultaneously or successively, in any order. In accordance with the invention, the characteristic feature of contact with the organometallic element M is that it is introduced in an aqueous solvent.

The precursor of element M can be selected from the group formed by halogen-containing compounds, hydroxides, oxides, carbonates and carboxylates of organometallic compounds of element M, this list not being limiting in nature. These compounds comprise at least one carbon-M bond. The precursor for element M can also be selected from compounds with general formula $(R_1)_xM(R_2)_y$ where x+y=the valency of metal M and where $R_1$ is selected from the group formed by alkyl, cycloalkyl, aryl, alkylaryl and arylalkyl functions, and $R_2$ is a function with formula $C_aH_bR'_c$, where R' represents a hydroxide, carboxylate, $PO_3H$ or $SO_3H$ function.

In one preferred preparation technique in accordance with the invention, the catalyst is obtained by impregnating the support using an aqueous or organic solution of at least one group VIII metal compound, the volume of the solution preferably being in excess with respect to the retention volume of the support, or equal to that volume. The impregnated support is then filtered, optionally washed with distilled water, then dried and calcined in air, normally between 110° C. and about 500° C., then reduced in hydrogen at a temperature which is normally in the range about 200° C. to about 600° C., preferably between about 300° C. and about 500° C. The product obtained is then impregnated with an aqueous solution of a compound of tin, germanium, lead, gallium, indium, gold, silver or thallium. Particularly advantageously, an aqueous solution of a carboxylate compound of tin is used, for example tributyl tin acetate.

After leaving the support impregnated with the group VIII metal in contact with the solution containing at least one compound of element M for several hours, the product is filtered, optionally washed with water, then dried. The operation is normally completed by calcining between 300° C. and 600° C., preferably in a stream of air for several hours. Before use, the catalyst is reduced in hydrogen, for example between 20° C. and 600° C., to obtain an active metal phase. The procedure for this treatment consists, for example, in slowly raising the temperature in a stream of hydrogen up to the maximum reduction temperature, for example in the range 20° C. to 600° C., preferably in the range 90° C. to 500° C., followed by maintaining that temperature for 1 to 6 hours, for example.

This reduction can be carried out immediately after calcining or later at the user's location. It is also possible to directly reduce the dried product at the user's location.

It is also possible to carry out prior reduction of the group VIII metal compound in solution using organic molecules with a reducing nature such as formic acid. The compound of additional element M can then be introduced simultaneously or successively. The solid can then be directly used when the catalytic reaction requires an aqueous solvent. A further possibility consists of filtering then drying the catalyst obtained. It can then be calcined followed by reduction under the conditions described above. It is also possible to carry out direct reduction from the dried product.

The following examples illustrate the invention without in any way limiting its scope.

EXAMPLE 1

Two catalysts A and B were prepared, comprising 1.3% by weight of rhodium and 1.5% by weight of tin. The support was an alumina with a specific surface area of 280 $m^2$ per gram.

Catalyst A (comparative)

Catalyst A was prepared using prior art techniques. 80 $cm^3$ of an aqueous solution of rhodium chloropentamine chloride was added to 100 g of alumina support. The catalyst was then dried at 110° C., calcined at 450° C. in air and reduced at 450° C. in a stream of hydrogen.

The catalyst was subsequently placed in a reactor containing heptane under hydrogen. Tetrabutyltin was injected at 20° C. The pressure was raised to 40 bars and the temperature to 100° C. After 20 minutes under these conditions, the reaction mixture was filtered, washed, dried and reduced at 450° C.

Catalyst B (in accordance with the invention)

Catalyst B was prepared using the techniques described above with the exception that the tin was introduced in the form of tributyltin acetate ($BU_3SnOC(O)CH_3$). 80 $cm^3$ of an aqueous rhodium chloropentamine chloride solution was added to 100 g of alumina support. The catalyst was dried at 110° C., calcined at 450° C. in air and reduced at 450° C. in a stream of hydrogen.

The catalyst was subsequently placed in a reactor containing an ammonia solution at pH 10 in hydrogen. The tributyl tin acetate was injected at 20° C. The pressure was raised to 40 bars and the temperature to 100° C. After 20 minutes under these conditions, the reaction mixture was filtered, washed, dried and reduced at 450° C.

EXAMPLE 2

Catalysts A and B were tested using a citral hydrogenation reaction in a perfectly stirred reactor under the following operation conditions:

feed: n-heptane+citral
temperature: 65° C.
pressure: 7.6 MPa
citral/rhodium: 200

The results obtained under these conditions are shown in Table 1. The yields are expressed in mole % after 5 hours of operation.

TABLE 1

| Catalysts | Conversion (%) | Selectivity (%) | | |
|---|---|---|---|---|
| | | Citronellol | Citronellal | Geraniol + nerol |
| A | 100 | 3.5 | 0.0 | 96.5 |
| B | 100 | 3.4 | 0.0 | 96.6 |

The performance of catalyst B prepared in accordance with the invention in an aqueous medium from an organometallic precursor was close to or even slightly superior than that of catalyst A. It enable citral (an unsaturated aldehyde) to be transformed into geraniol and nerol (the corresponding unsaturated alcohols) with limited formation of citronellol (the corresponding alcohol).

EXAMPLE 3

Two catalysts C and D were prepared, comprising 1.1% by weight of rhodium and 2.2% by weight of tin. The support was an alumina with a specific surface area of 280 $m^2$ per gram.

Catalyst C (comparative)

Catalyst C was prepared using prior art techniques. 80 cm$^3$ of an aqueous solution of rhodium chloropentamine chloride was added to 100 g of alumina support. The catalyst was then dried at 110° C., calcined at 450° C. in air and reduced at 450° C. in a stream of hydrogen.

The catalyst was subsequently placed in a reactor containing heptane under hydrogen. Tetrabutyltin was injected at 20° C. The pressure was raised to 40 bars and the temperature raised to 100° C. After 20 minutes under these conditions, the reaction mixture was filtered and dried under nitrogen at 110° C.

Catalyst D (in accordance with the invention)

Catalyst D was prepared using the techniques described above with the exception that the tin was introduced in the form of tributyltin acetate ($Bu_3SnOC(O)CH_3$). 80 cm$^3$ of an aqueous rhodium chloropentamine chloride solution was added to 100 g of alumina support. The catalyst was dried at 110° C., calcined at 450° C. in air and reduced at 450° C. in a stream of hydrogen.

The catalyst was subsequently placed in a reactor containing an ammonia solution at pH 10. The tributyl tin acetate was injected at 20° C. The pressure was raised to 40 bars and the temperature to 100° C. After 20 minutes under these conditions, the reaction mixture was filtered and dried under nitrogen at 110° C.

EXAMPLE 4

Catalysts C and D were tested using a nitrobenzene hydrogenation reaction in a perfectly stirred reactor under the following operating conditions:

feed: ethanol+nitrobenzene temperature: 30° C.

pressure: 2.0 MPa nitrobenzene/rhodium: 200

The results obtained under these conditions are shown in Table 2. The yields are expressed in mole % after 3 hours of operation.

TABLE 2

| Catalysts | Conversion (%) | Aniline selectivity (%) |
| --- | --- | --- |
| C | 97 | 98 |
| D | 97 | 98 |

The performance of catalyst D prepared in accordance with the invention in an aqueous medium from an organometallic precursor was close to that of catalyst C on hydrogenation of the nitrogen-containing compound to the corresponding amine.

The results obtained under these conditions are shown in Table 2. The yields are expressed in mole % after 3 hours of operation.

TABLE 2

| Catalysts | Conversion (%) | Aniline selectivity (%) |
| --- | --- | --- |
| C | 97 | 98 |
| D | 97 | 98 |

The performance of catalyst D prepared in accordance with the invention in an aqueous medium from an organometallic precursor was close to that of catalyst C on hydrogenation of the nitrogen-containing compound to the corresponding amine.

The preceding examples can be repeated with similar success by substituting the generically or specifically described reactants and/or operating conditions of this invention for those used in the preceding examples.

The entire disclosure of all applications, patents and publications, cited above, and of corresponding French application No.97/13.688, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process comprising:

preparing a catalyst comprising at least one support, at least one metal from group VIII of the periodic table and at least one additional element M selected from the group consisting of germanium, tin, lead, rhenium, gallium, indium, gold, silver and thallium, wherein said additional element M is in the form of at least one water-soluble organometallic compound containing at least one carbon-M bond, the preparation of said catalyst comprising introducing an aqueous solution of said organometallic compound into said support, and contacting said catalyst in a dried, calcined and reduced form with an organic compound containing at least one function selected from an aldehyde, ketone, ester, acid or nitro function and/or containing an aromatic group, in the presence of said hydrogen so as to hydrogenate said organic compound.

2. A process according to claim 1, in which the catalyst further contains at least one alkali or alkaline-earth metal.

3. A process according to claim 1, in which the catalyst further contains at least one metalloid.

4. A process according to claim 1, in which the catalyst further contains at least one halogen or halogen-containing compound.

5. A process according to claim 1 in which in the catalyst, the group VIII metal is iridium, nickel, palladium, platinum, rhodium or ruthenium.

6. A process according to claim 1 in which in the catalyst, element M is germanium or tin.

7. A process according to claim 1 in which the catalyst, the organometallic compound of element M is selected from the group consisting of hydroxides, halogen-containing compounds, and carboxylates f organic compounds of element M, compounds with general formula $(R_1)_xM(R_2)_y$ where x+y=the valency of metal M and where $R_1$ is selected from the group formed by alkyl, cycloalkyl, aryl, alkylaryl and arylalkyl functions, and $R_2$ is a function with formula $C_aH_bR'_c$, where R' represents a hydroxide, carboxylate, $PO_3H$ or $SO_3H$ function.

8. A process according to claim 7, in which in the catalyst, the organometallic compound of element M is selected from the group formed by carboxylates of organic compounds of element M.

9. A process according to claim 8, in which in the catalyst, the organometallic compound of element M is tributyltin acetate.

10. A process according to claim 1, in which during preparation of the catalyst, the group VIII metal, additional element M in the form of a water-soluble organometallic compound, optional halogen or halogen-containing compound, optional alkali or alkaline-earth metal, and optional metalloid are introduced into the support successively or simultaneously.

11. A process according to claim 1, in which the catalyst is prepared by carrying out the following steps in any order:
impregnating a support using an aqueous or organic solution of at least one group VIII metal, filtering, drying, calcining, and reducing;
impregnating the product obtained using an aqueous solution of at least one organometallic compound of additional element M, filtering, drying, optionally reducing, then calcining.

12. A process according to claim 1, in which when preparing the catalyst, additional element M in the form of a water-soluble organometallic compound is introduced during production of the support.

13. A process according to claim 1, in which the catalyst is reduced in hydrogen at a temperature in the range 20° C. to 600° C.

14. A process according to claim 13, in which prior reduction of the group VIII metal compound is carried out is solution by an organic reducing agent.

15. A process according to claim 1, in which the feed to be treated is brought into contact with the catalyst at a pressure in the range 0.1 MPa to 10 MPa and at a temperature in the range 10° C. to 800° C. with a space velocity in the range 0.1 to 100 volumes of liquid feed per hour per volume of catalyst and at a space velocity in the range 0.5 to 50 volumes of liquid feed per hour per volume of catalyst.

16. A process according to claim 5, wherein the group VIII metal is platinum, palladium, ruthenium, or rhodium.

17. A process according to claim 14, wherein the organic reducing agent is formic acid.

18. A process according to claim 1, wherein the organic compound to be hydrogenated has a nitro function.

19. A process according to claim 13, wherein the temperature is 90° C. to 500° C.

20. A process according to claim 13, wherein the temperature is 10° C. to 500° C.

21. A process according to claim 1, wherein said organic compound is an aldehyde.

22. A process according to claim 1, wherein said organic compound has a nitro function.

* * * * *